(12) United States Patent
Francisco et al.

(10) Patent No.: US 7,526,960 B2
(45) Date of Patent: May 5, 2009

(54) PRESSURE TRANSMITTING CONNECTOR FOR AN ENDOSCOPY SYSTEM

(75) Inventors: Andre Francisco, Sophia Antipolis (FR); Patrick Janin, Nice (FR); Thierry Pascual, Cagnes-sur-Mer (FR); Armando Dias, Saint Laurent du Var (FR)

(73) Assignee: Future Medical System S.A., Meyrin (CH)

( * ) Notice: Subject to any disclaimer, the term of this patent is extended or adjusted under 35 U.S.C. 154(b) by 60 days.

(21) Appl. No.: 10/591,753

(22) PCT Filed: Mar. 3, 2005

(86) PCT No.: PCT/CH2005/000127

§ 371 (c)(1),
(2), (4) Date: Dec. 21, 2006

(87) PCT Pub. No.: WO2005/084524

PCT Pub. Date: Sep. 15, 2005

(65) Prior Publication Data

US 2007/0186660 A1    Aug. 16, 2007

(30) Foreign Application Priority Data

Mar. 4, 2004   (FR) .................................. 04 02238

(51) Int. Cl.
*G01L 7/08* (2006.01)
(52) U.S. Cl. .................... 73/715; 73/716; 73/729.2
(58) Field of Classification Search ........... 73/700–756; 361/283.1–283.4
See application file for complete search history.

(56) References Cited

U.S. PATENT DOCUMENTS

| | | | |
|---|---|---|---|
| 4,086,815 A * | 5/1978 | Asano et al. ................. 73/721 |
| 4,132,227 A | 1/1979 | Ibe | |
| 5,037,386 A | 8/1991 | Marcus et al. | |
| 5,044,203 A | 9/1991 | Wiest et al. | |
| 5,097,712 A * | 3/1992 | Gerst et al. ................. 73/708 |
| 5,643,203 A | 7/1997 | Beiser et al. | |
| 5,810,770 A | 9/1998 | Chin et al. | |
| 6,086,542 A | 7/2000 | Glowa et al. | |

OTHER PUBLICATIONS

International Search Report mailed May 10, 2005 of International Application PCT/CH2005/000127.

* cited by examiner

*Primary Examiner*—Andre J Allen
*Assistant Examiner*—Jermaine Jenkins
(74) *Attorney, Agent, or Firm*—Westerman, Hattori, Daniels & Adrian, LLP.

(57) ABSTRACT

The inventive pressure transmitting connector, in particular for an endoscopy system includes a fluid transporting channel, a blind compartment which opens towards the transport channels by a pipe and closed by a membrane which is deformable according to a pressure in the transport channels and a device for transmitting a representative quantity of the pressure in the transport channel according to the membrane deformation. The transport channel, the pipe and the blind compartment are embodied in the same rigid part to which the membrane is attached. In a preferred embodiment, the membrane simultaneously closes the blind compartment and a pressure transmitting chamber attached to the rigid part.

7 Claims, 7 Drawing Sheets

PRESSURE TRANSMITTING CONNECTOR FOR AN ENDOSCOPY SYSTEM

TECHNICAL FIELD

The invention relates to a pressure-sensing connector intended more particularly for an endoscopy system, comprising a fluid communication path, a blind compartment opening onto the communication path via a duct and closed off by a membrane that deforms according to the pressure in the communication path, and a means for transmitting the deformation of the membrane in the form of a quantity representative of the pressure in the communication path.

PRIOR ART

An endoscopy system comprising more particularly a cannula for housing an endoscope and for forming, between the cannula and the endoscope, an irrigation or outflow channel, is described for example by documents U.S. Pat. Nos. 5,037,386 and 6,086,542. The system also includes a coupling ring mounted around the cannula and provided with a coupling path for communicating with the irrigation or outflow channel. It is used in joint arthroscopy and more particularly in knee arthroscopy. The endoscope is connected to a video screen in order to display the joint. The irrigation or outflow channel makes it possible to create a circulation of physiological saline in order to keep the medium in front of the endoscope optically clear and to bathe the joint. The circulation is provided by a pump connected to a reservoir and discharging into a tubing connected to the irrigation or outflow channel via the coupling ring.

The pressure of the physiological saline in the joint is controlled by a membrane pressure sensor placed in a tubing connected via the coupling ring to a channel formed in the cannula and dedicated to pressure sensing.

This arrangement has the drawback of resulting in the pressure being erroneously determined under certain operating conditions, for example by accident there is a sharp bend in the tubing between the pressure sensor and the coupling ring.

Document U.S. Pat. No. 5,044,203 discloses a membrane pressure sensor to be connected to such a tubing. The sensor comprises a rigid communication path provided with an opening for communicating with a blind compartment in the form of a flexible tube connected around the communication path. Two oil-filled chambers are placed around the blind compartment in such a way that two membranes fixed to the transmission chambers are brought into contact with two portions of the blind compartment consisting of two other membranes. A fluid circulating in the communication path enters the blind compartment via the opening and deforms the membranes of the blind compartment and of the two transmission chambers. The oil pressure, which depends on the deformation of the membranes, is transmitted to sensors mounted on each oil pressure chamber in order to determine the pressure in the communication path.

This arrangement has the drawback in which the blind compartment in the form of a flexible tube may itself be deformed on its walls and thus introduce a source of error in the determination of the pressure compared with what it would be if the deformation of the membranes were to result only from the effect of the pressure in the communication path.

Document U.S. Pat. No. 5,643,203 discloses an endoscopy system of the type mentioned above, in which a connector is mounted on the coupling ring and comprises a communication path for communicating with the irrigation channel and a pressure sensor for sensing the pressure in the communication path. The pressure of the physiological saline in the joint is extrapolated using a law based on the pressure sensed in the communication path.

The extrapolation of the pressure in the joint on the basis of the pressure sensed in the communication path of the connector makes it possible to dispense with one channel in the cannula dedicated for pressure sensing. Thus it is possible to decrease the diameter of the cannula, for the purpose of reducing the trauma when it is being introduced into the joint. Compared to a tubing, the connector thus eliminates the risk of a variation in cross section of the communication path and allows reliable sensing of the pressure in this communication path.

The connector is a rigid part comprising a fluid communication path and a duct perpendicular to the communication path. A pressure sensor is attached to the connector. It comprises a blind compartment designed to be placed facing the duct so as to open into the communication path. A membrane placed in the blind compartment is connected to a piezoelectric transducer in order to convert a deformation due to the pressure in the communication path into an electrical voltage.

This arrangement has the drawback whereby, during assembly, it is necessary for the duct formed in the connector and the blind compartment formed in the piezoelectric transducer sensor to be positioned precisely.

The object of the invention is to modify a connector known from the prior art, illustrated above, in order to simplify the assembly.

DISCLOSURE OF THE INVENTION

For this purpose, the subject of the invention is a pressure-sensing connector intended more particularly for an endoscopy system, comprising a fluid communication path, a blind compartment that opens onto the communication path via a duct and is closed off by a membrane that deforms according to the pressure in the communication path, and a means for transmitting a quantity representative of the pressure in the communication path according to the deformation of the membrane, characterized in that the communication path, the duct and the blind compartment are formed in the same rigid part to which the membrane is attached.

Mounting the membrane on the blind compartment, in order for the latter to be closed off, simplifies the assembly of the connector according to the invention. In addition, the rigid part, in which the communication path, the duct and the blind compartment are formed, can be easily cleaned before mounting the membrane. Finally, the fully assembled connector is easily sterilized.

In a preferred embodiment of the invention, the membrane closes off both the blind compartment and a pressure-transmitting chamber, preferably filled with air and connected to the rigid part, in order to transmit the deformation of the membrane in the form of an air pressure. Compared to a piezoelectric transducer, this arrangement eliminates the risk of any deterioration during an operation to sterilize the connector. Compared to oil transmission, this arrangement also eliminates the risks of contaminating the blind compartment and the communication path of the connector, and also the irrigation or outflow channel.

BRIEF DESCRIPTION OF THE DRAWINGS

The invention will become apparent on reading the description of one embodiment illustrated below by the drawings.

EMBODIMENTS OF THE INVENTION AND INDUSTRIAL APPLICATION

Figure 1:
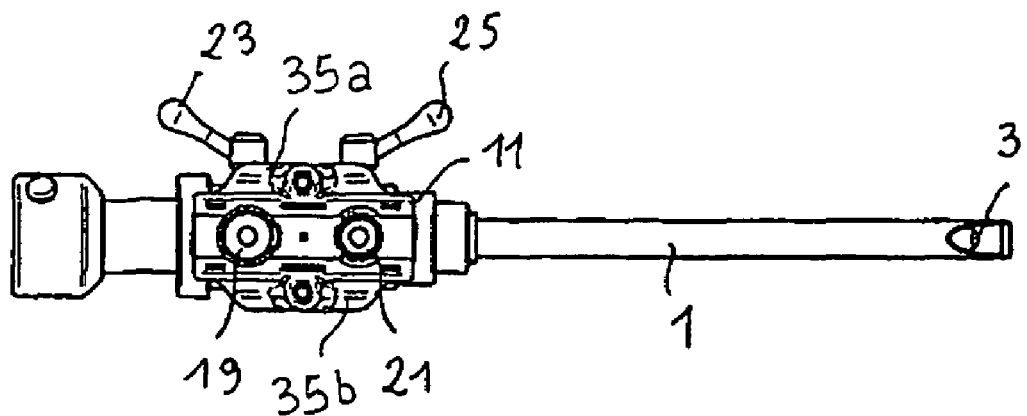
FIG. 1 shows an endoscopy system in front view.
Figure 2:
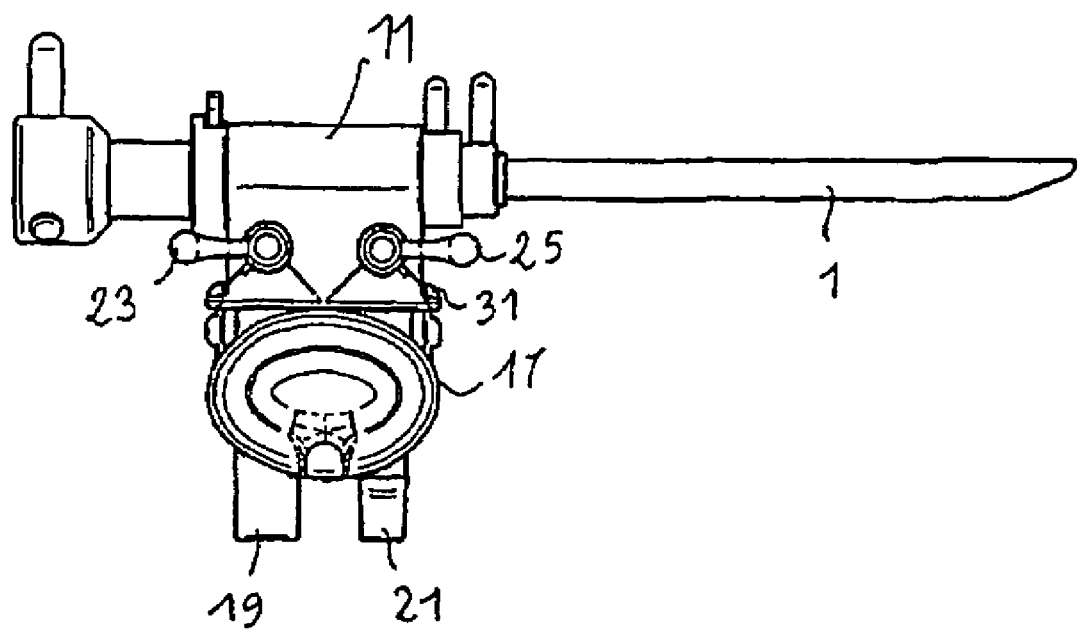
FIG. 2 shows the endoscopy system of FIG. 1 in top view.
Figure 3:
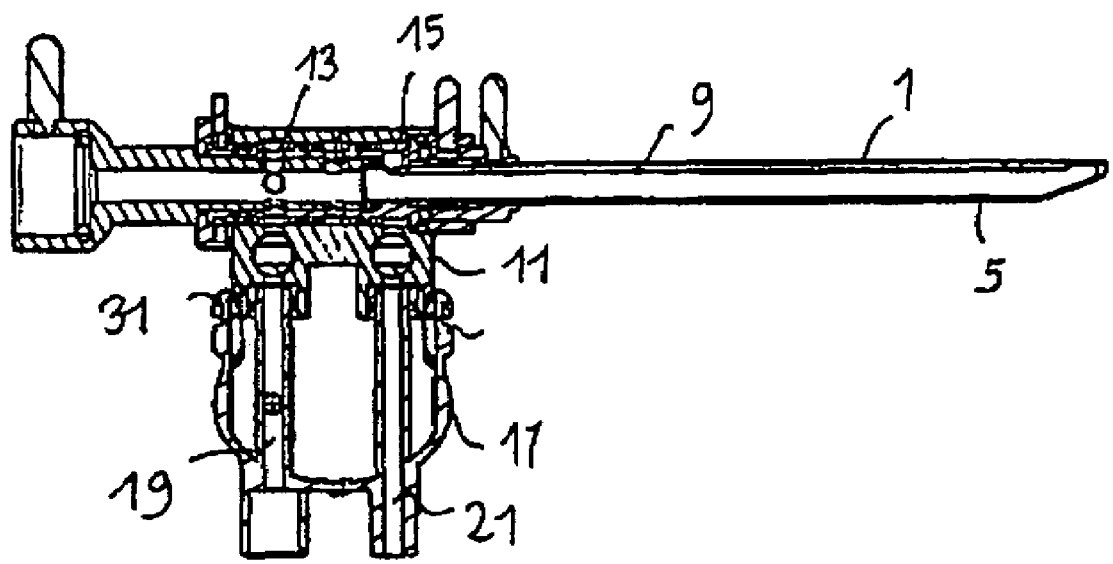
FIG. 3 shows the endoscopy system of FIG. 1 in longitudinal section.
Figure 4:
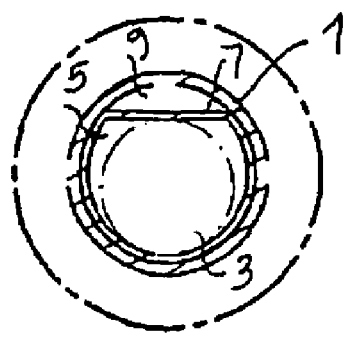
FIG. 4 shows the endoscopy system of FIG. 1 in cross section.

An endoscopy system comprises (FIGS. 1 to 4) a cannula 1 for housing an endoscope 3 and for forming, between the cannula 1 and the endoscope 3, an irrigation channel 5. In the embodiment illustrated by the figures, the irrigation channel 5 is formed between the endoscope 3 and a tube 7 internal to the cannula 1, and an outflow channel 9 is formed between the internal tube 7 and the cannula 1.

A coupling ring 11 is mounted around the cannula 1 in order to communicate with the irrigation channel 5 and the outflow channel 9. A first coupling path 13 communicates with the irrigation channel 5. A second coupling path 15 communicates with the outflow channel 9.

A connector 17 is mounted on the coupling ring 11. It comprises a first communication path 19, for communicating with the first coupling path 13 at the irrigation channel 5, and a second communication path 21, for communicating with the second coupling path 15 at the outflow channel 9. A blind compartment 39a, 39b opens onto each communication path 19, 21 via a duct 41a, 41b. A transmission chamber 35a, 35b provided with a membrane 37a, 37b is designed so that a pressure in the communication path 19, 21 is transmitted to the transmission chamber 35a, 35b by deformation of the membrane.

Tubings (not shown) are connected to the communication paths 19 and 21 of the connector 17 and are connected to a pump in order to create a flow of fresh physiological saline in the irrigation channel 5 and of soiled physiological saline in the outflow channel 9. The coupling ring 11 comprises, in a manner known per se, taps 23 and 25 for opening or closing the coupling paths 13 and 15 according to the desired flow in the irrigation channel 5 or in the outflow channel 9.

The connector 17 is mounted on the coupling ring 11 so as to allow the irrigation channel 5 and the outflow channel 9 to communicate with the communication paths 13 and 15 of the connector via a tubing. With this arrangement, the pressure sensed in one or other communication path of the connector is not subject to an error due to an accidental variation in the cross section of the tubings that would be connected to the coupling paths of the coupling ring.

The communication path 19, 21, the duct 41a, 41b and the blind compartment 39a, 39b are formed in the same rigid part 43 to which the membrane 37a, 37b and the transmission chamber are connected, in order to close off the transmission chamber on the blind compartment 39a, 39b by the membrane 37a, 37b.

Figure 5:
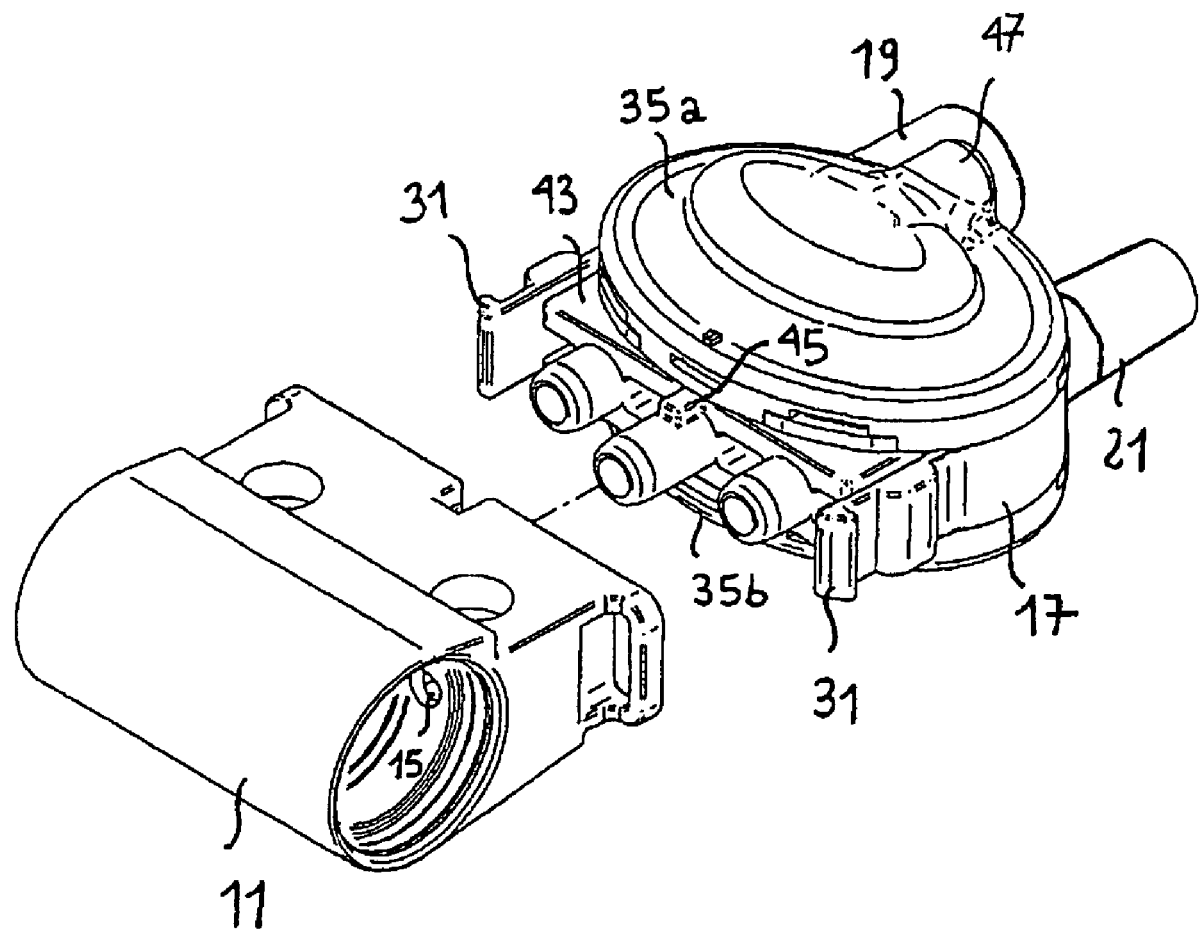
FIG. 5 shows, in perspective, a connector according to the invention in the position for being connected to a coupling ring of an endoscopy system according to FIGS. 1 to 4.

The rigid part 43 is provided with fastening means 31 for reversibly connecting (FIG. 5) the connector 17 to the coupling ring 11. Preferably, the rigid part 43 is provided with a polarizing feature 45, which polarizes the connection to the coupling ring 11. These arrangements allow a surgeon to connect the connector to the coupling ring in an easy and reliable manner.

The physiological saline flowing in the communication path 19 with the irrigation channel 5, or in the communication path 21 with the outflow channel 9, enters the blind compartment 39a, 39b closed off by the membrane 37a, 37b. The latter 37a, 37b deforms according to the pressure of the physiological saline in the communication path 19 or 21. This deformation causes a variation in the air pressure inside the transmission chamber 35a, 35b. Capillaries (not shown) are connected to connection points 47 of the transmission chambers 35a, 35b in order to transmit the pressure variation to sensors (not shown) and to determine the pressure of the physiological saline in each of the communication paths 19, 21.

The pressure of the physiological saline in the joint is extrapolated using a law based on the pressure sensed in the communication path. Preferably, a relationship between the fluid flow rate is used, given by the speed of rotation of the irrigation pump, or the outflow pump, and a pressure drop, determined experimentally, between the communication path of the connector and the mouth of the irrigation or outflow channel.

Figure 6:
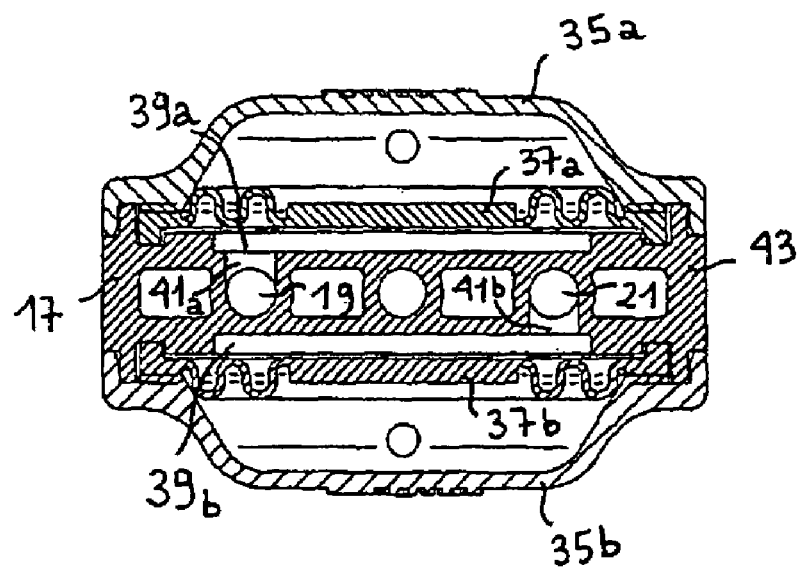
FIG. 6 shows a cross section of a first connector intended for an endoscopy system according to the invention.

In FIG. 6, each blind compartment 39a, 39b opens onto each respective communication path 19, 21. This arrangement allows the pressure in each communication path 19, 21 to be sensed independently. In this embodiment of the invention, the connector 17 allows, in the endoscopy system described above, two determinations of the pressure of the physiological saline in the joint, by extrapolation on the basis of the pressure sensed in the communication path 19 with the irrigation channel 5 on the one hand, and in the communication path 21 with the outflow channel 9 on the other. Advantageously, the pressure in the joint may be extrapolated by means of one 19 of the two communication paths even when the circulation of the physiological saline is interrupted in the other 21 communication path by closing the irrigation tap 23, or outflow tap 25 respectively. Also in this arrangement, the surgeon advantageously connects the coupling ring, in a single operation, to the communication path for irrigation and to the communication path for outflow, while still being able to sense the pressure in each of these two channels.

The two pressure taps on the two communication paths of the connector allow the integrity of the endoscopy system described above to be better checked, by comparing the sensed pressures with expected values obtained experimentally. Should there be a difference, a fault in the irrigation tap 23 or the outflow tap 25 may be diagnosed, or else the presence of a foreign body in the irrigation channel or in the outflow channel may be diagnosed. Advantageously, these checks will be made by the surgeon at the start of use of the endoscopy system.

Figure 7:
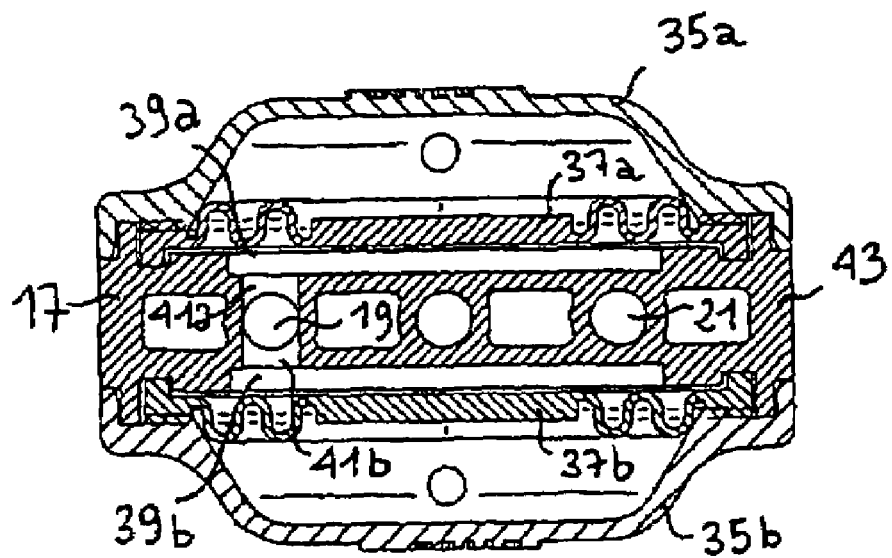
FIG. 7 shows, in cross section, a second connector intended for an endoscopy system according to the invention.

In FIG. 7, the two blind compartments 39a, 39b open onto the same communication path, for example 19. This arrangement allows double sensing of the pressure in the communication path 19.

Preferably, the rigid part 43 is manufactured by the injection molding of a plastic. This method of manufacture is advantageous in order to obtain single-use connectors.

The invention claimed is:

1. A pressure-sensing connector intended more particularly for an endoscopy system, comprising:
   two fluid communication paths,
   two blind compartments, each of said blind compartments opening onto one of the communication paths and being closed off by a respective membrane that deforms according to the pressure in the respective communication path, and a means for transmitting quantities representative of the pressure in each of said communication paths according to the deformation of the respective membrane, wherein each blind compartment opens onto its respective communication path via a respective duct, wherein the communication paths, the ducts and the blind compartments are formed in the same rigid part to which the membranes are attached, and wherein said membranes move independently from one another so that the pressure in each blind compartment can be sensed independently.

2. The connector as claimed in claim 1, wherein the two blind compartments open onto the same communication path.

3. The connector as claimed in claim 1, wherein each membrane closes off both said respective blind compartment and a respective pressure-transmitting chamber, connected to the rigid part, in order to convert the deformation of each membrane into a pressure representative of the pressure in the respective communication path.

4. The connector as claimed in claim 3, wherein the pressure-transmitting chambers are totally filled with air in order to convert the deformations of the membranes into air pressures.

5. The connector as claimed in claim 1, wherein the rigid part is provided with a polarizing feature.

6. The connector as claimed in claim 1, wherein the rigid part is made of injection-molded plastic.

7. The connector as claimed in claim 1, wherein said communication paths are located on a same side of the connector so that they can be connected in a single operation to a coupling ring.

* * * * *